(12) United States Patent
Boucneau et al.

(10) Patent No.: US 12,609,193 B2
(45) Date of Patent: Apr. 21, 2026

(54) SYSTEMS AND METHODS FOR A MULTI-PARAMETER SAMPLING TOOL

(71) Applicant: GE Precision Healthcare LLC, Wauwatsoa, WI (US)

(72) Inventors: Tanguy Thierry Boucneau, Versailles (FR); Sofiene Bourghes, Paris (FR); Nicolas Gogin, Chatenay-Malabry (FR); Adeline Digard-Bahuon, Bonnelles (FR); Jorge Eduardo Hernandez Londono, Versailles (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 505 days.

(21) Appl. No.: 18/105,109

(22) Filed: Feb. 2, 2023

(65) Prior Publication Data

US 2024/0266029 A1     Aug. 8, 2024

(51) Int. Cl.
*G16H 30/40* (2018.01)
*G06F 3/04845* (2022.01)
*G06F 3/04847* (2022.01)
*G06T 5/20* (2006.01)
*G06T 5/40* (2006.01)
*G06V 10/75* (2022.01)
*G06V 10/762* (2022.01)
*G16H 30/20* (2018.01)

(52) U.S. Cl.
CPC ......... *G16H 30/40* (2018.01); *G06F 3/04845* (2013.01); *G06F 3/04847* (2013.01); *G06T 5/20* (2013.01); *G06T 5/40* (2013.01); *G06V 10/758* (2022.01); *G06V 10/762* (2022.01); *G16H 30/20* (2018.01); *G06T 2207/20104* (2013.01)

(58) Field of Classification Search
CPC ............................................ G06T 2207/20081
See application file for complete search history.

(56) References Cited

U.S. PATENT DOCUMENTS

| | | | |
|---|---|---|---|
| 5,542,003 A | 7/1996 | Wofford | |
| 5,615,320 A | 3/1997 | Lavendel | |

(Continued)

FOREIGN PATENT DOCUMENTS

| | | | | |
|---|---|---|---|---|
| CN | 109646033 A | * | 4/2019 | ............. A61B 6/037 |
| GB | 2562342 A | | 11/2018 | |
| WO | 2013156066 A1 | | 10/2013 | |

*Primary Examiner* — Di Xiao
(74) *Attorney, Agent, or Firm* — Fletcher Yoder, P.C.

(57) ABSTRACT

A system may include a processor-based device storing or accessing an image review application, which when executed by the processor-based device, causes acts to be performed such as retrieving image data for populating a graphical user interface displayed on the processor-based device and receiving a user input selecting a workflow tool and a sampling tool. The sampling tool, when executed by the processor-based device, may also receiving an additional user input of a region of interest within the image data, determining values for a parameter of interest based on the pixels within the region of interest, automatically configuring the workflow tool based on the determined values for the parameter of interest, and generating preset parameters of the workflow tool. The image review application may also adjust the display of the image data on the GUI using the configured workflow tool.

12 Claims, 10 Drawing Sheets

(56)        References Cited

U.S. PATENT DOCUMENTS

| | | | |
|---|---|---|---|
| 7,218,763 B2 | 5/2007 | Belykh et al. | |
| 7,424,142 B2 | 9/2008 | Arnold | |
| 8,094,879 B2 | 1/2012 | Kalla et al. | |
| 11,030,742 B2 | 6/2021 | Knoplioch et al. | |
| 11,748,066 B1 * | 9/2023 | Good | G06F 8/34 |
| | | | 717/105 |
| 2009/0213136 A1 | 8/2009 | Desjardins et al. | |
| 2016/0086324 A1 * | 3/2016 | Bozkurt | G03F 7/70633 |
| | | | 382/145 |
| 2016/0171689 A1 | 6/2016 | Lee et al. | |
| 2017/0200473 A1 * | 7/2017 | Moore | H04N 21/41407 |
| 2018/0285531 A1 * | 10/2018 | Korn | G16H 50/30 |
| 2019/0147639 A1 | 5/2019 | Sudarsky et al. | |
| 2019/0282213 A1 * | 9/2019 | Cheung | G06F 3/04847 |
| 2021/0327563 A1 * | 10/2021 | He | G06N 3/045 |
| 2022/0108506 A1 * | 4/2022 | Gupta | G06V 40/171 |
| 2023/0091962 A1 * | 3/2023 | Lee | G06N 3/09 |
| | | | 216/59 |
| 2023/0177680 A1 * | 6/2023 | Adsul | G06T 7/0012 |
| | | | 348/222.1 |
| 2024/0005653 A1 * | 1/2024 | Degen | G06V 10/25 |

* cited by examiner

SYSTEMS AND METHODS FOR A MULTI-PARAMETER SAMPLING TOOL

BACKGROUND

The subject matter disclosed herein relates to medical imaging, and more particularly, to systems and methods for automatically setting or adjusting preset settings of one or more parameters of a tool based on pixel and/or content data extracted from a region of interest within an image.

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Non-invasive imaging technologies allow images of the internal structures or features of a subject to be obtained non-invasively. In particular, non-invasive imaging technologies rely on various physical principles, such as the differential transmission of X-rays through the target volume or the reflection of acoustic waves, to acquire data and to construct images or otherwise represent the internal features of the subject. By way of example, in X-ray based imaging technologies, signals representative of an amount or an intensity of radiation may be collected, and the signals may then be processed to generate an image that may be displayed for review.

When reviewing images, a user (e.g., radiologist) may perform one or more actions on and/or with the image in order to make an assessment, provide feedback, and/or make a diagnosis. For example, the user may change a contrast of the image with a first tool and determine a size of a vessel with a second tool. Additionally, the user may adjust a brightness and/or grayscale of the image with a third tool. However, the user determines or accepts a setting for each of the tools used to make an accurate assessment, which may increase an amount of time needed to review the image. Moreover, each setting of each tool may be manually adjusted by the user, thereby increasing a likelihood of human error as well as increasing the time involved. Thus, improvements for medical image reviews are desired to decrease turn-around time, decrease operational costs, and improve quality of service delivered.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, a system may include a processor-based device storing or accessing an image review application, which when executed by the processor-based device, causes acts to be performed such as retrieving image data for populating a graphical user interface (GUI) displayed on the processor-based device and receiving a user input selecting a workflow tool and a sampling tool. The sampling tool, when executed by the processor-based device, may cause acts to be performed such as receiving an additional user input of a region of interest within the image data, determining values for a parameter of interest based on the pixels within the region of interest, and automatically configuring the workflow tool based on the determined values for the parameter of interest. The image review application may also cause acts to be performed such as generating preset parameters of the workflow tool and adjusting the display of the image data on the GUI using the configured workflow tool.

In an embodiment, a method may include receiving, via a processor, a medical image for populating a graphical user interface (GUI) to display for a user, receiving a first user input selecting a sampling tool, and receiving a second user input from the sampling tool of a region of interest within the medical image. The method may also include determining, via the processor, a value or values for a parameter of interest based on pixels within the region of interest, automatically configuring a workflow tool based on the determined value or values for the parameter of interest, and applying the configured workflow tool to adjust the display of the medical image on the GUI.

In an embodiment, a non-transitory, computer-readable medium comprising computer-readable code, that when executed by one or more processors, causes the one or more processors to perform operations including receiving image data for populating a graphical user interface (GUI) to display for a user, receiving a user input selecting a workflow tool and a sampling tool, and receiving an additional user input from the sampling tool of an anatomical region within the image data. The one or more processors may also perform operations including determining a value or values for a parameter of interest based on pixels associated with the anatomical region, dynamically configuring the workflow tool based on the determined value or values for the parameter of interest, and implementing the configured workflow tool to adjust the display of the image data on the GUI.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
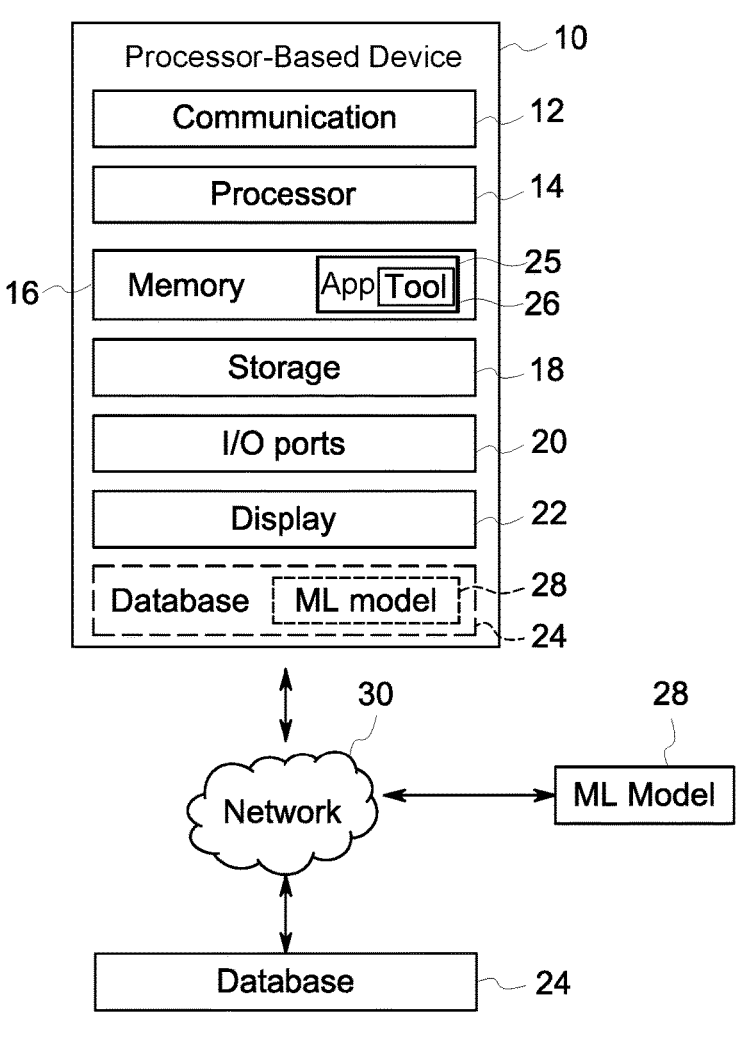
FIG. 1 illustrates a block diagram of a processor-based system, such as a workstation or server, that may be used in implementing an image review application including a sampling tool, in accordance with aspects of the disclosure.

One or more specific embodiments of the present disclosure are described above. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision herein of examples and explanations in such a medical context is only to facilitate explanation by providing instances of real-world implementations and sampling tools. However, the present approaches may also be utilized in other contexts, such as workflows related to editing and exporting photography images (e.g., photoshopping images), reviewing microscopy images (e.g., optical microscopy, electronic microscopy, scanning probe microscopy), reviewing images for inspection of objects (e.g., security screening for packages, boxes, luggage), editing and exporting images for industrial design (e.g., computer-aided design, 3D modeling), and so on.

By way of example, a radiology workflow may include several actions such as ordering, annotating, scheduling, image acquisition, storage, and viewing activities associated with radiology exams. Following image acquisition, a user (e.g., radiologist) may perform image and data analysis (e.g., interpretation) to make a diagnosis, prescribe or suggest a future treatment, and/or report a result. To this end, in conventional approaches the user may utilize one or more workflow tools to perform the workflow (e.g., review). For example, the user may use a viewing tool to adjust a window width and a window level to view the image. In another example, the user may configure one or more parameters by adjusting or specifying a value for that parameter (e.g., a set point, setting, parameter value) on a brush panel to regularize a size of the selected anatomy and/or adjust thresholds for the brush tool to properly annotate, label, or segment the selected anatomy. However, the user may test one or more parameters before finding an optimal parameter or setting for the selected workflow tool. In certain instances, the user may not find optimal parameter(s), thus impacting the quality of service delivered. Additionally or alternatively, switching between each of the workflow tools in such conventional approaches not only increases an amount of time needed to review the image and make the diagnosis, but also introduces human error into the review. As such, operational costs may increase while turn-around time decreases.

Embodiments of the present disclosure address certain of these issues and are directed to a multi-parameter sampling tool integrated with an image review application of a processor-based device to decrease read time and error by identifying a subset of pixels from a selected region of interest within a medical image and automatically configuring (e.g., setting, suggesting, adjusting) one or more parameters of a workflow tool based on the selection. For example, the user may review an image on a workstation and utilize the sampling tool to improve a workflow process. While reviewing, the user may use the sampling tool to select a region of interest by user input, such as a mouse click, one or more mouse clicks, or a touch via a touch screen on the workstation. The sampling tool employed by the user may receive the user input and extract one or more values from the pixels of the selected (e.g., sampled) region of interest. For example, the values may include a total number of pixels within the region of interest, a grayscale value or median or mean grayscale value, an intensity value or median or mean intensity value, a density value or median or mean density value, a color value (e.g., an RGB value or scale), a threshold segmentation value, and the like. In another example, the sampling tool may compute statistics or plots (e.g., histogram, graphs, charts, pixel contrast) based on the subset of pixels from the selected region of interest. Then, the sampling tool may automatically configure the parameters for a workflow tool (e.g., a visualization tool, an annotation tool) by specifying a value for that parameters (e.g., set point, setting, parameter value) based on the extracted and/or computed values or data derived from the selected pixels. In certain instances, the sampling tool may automatically configure parameters for one or more workflow tools. Additionally or alternatively, the sampling tool may automatically adjust the image by applying a mask to the image or directly adjusting the pixels of the image. In this way, the sampling tool may reduce a number of work-flow steps performed by the user during the review. Additionally or alternatively, the sampling tool may optimize values for each parameter of the workflow tool (e.g., a review tool, a segmentation tool, an annotation or labeling tool, a visualization or display tool, a parameter tool, and so forth). As such, the sampling tool may improve the work-flow for the user, improve quality of service delivered, and decrease operational costs.

The sampling tool may learn, such as via-machine-learning routines, to set one or more parameters of the other workflow tools based on user feedback or selections. For example, the sampling tool, when used to sample or select a region of pixels, may be used to configure one or more parameters for the workflow tool and the user may further adjust the parameters, or not, as needed. The user feedback (e.g., adjustment) may be stored in a database as historical user data and the sampling tool may be trained with the historical user data. In another example, the sampling tool may perform a characterization (e.g., analysis) based on the subset of pixels from the selected or sampled region of interest and the user may adjust the pixels. For instance, the user may remove outlier pixels from the analysis. In other instances, the sampling tool may generate a histogram with one or more histogram curves based on the subset of pixels and the user may select one histogram curve from the one or more histogram curves for robust characterization. Based on the user feedback (e.g., user input), the sampling tool may adjust the parameters of the workflow tool.

With the preceding in mind, FIG. 1 illustrates an embodiment of a processor-based device 10 for acquiring and processing image data, in accordance with aspects of the present disclosure. The processor-based device 10 may receive raw or pre-processed image data from one or more data sources and process the signals into image data via signal processing techniques, machine-learning routines, artificial intelligence, and so on. The processor-based device 10 may also receive processed or pre-processed image data and perform image visualization techniques. For example, a user (e.g., radiologist) may use the processor-based device 10 to view images, annotate, analyze, store, print, send, or otherwise manipulate the image data. To this end, the processor-based device 10 may 10 may include any suitable computer device, such as a general-purpose personal computer or workstation (e.g., review station), a server, a laptop computer, a tablet computer, a mobile computer, and the like that includes specific computer-readable instructions in accordance with present embodiments. In an embodiment, the processor-based device 10 may include or communicate with a picture archiving and communications system (PACS) that may store and transmit information captured by medical imaging. For example, the information may include image data such as computed tomography (CT), X-ray imagery, positron emission tomography (PET), single-photon emission computed tomography (SPECT), tomosynthesis, mammography, fluoroscopy, magnetic resonance imaging (MRI), and so on. The PACS may in turn be coupled to a remote client, a radiology department information system (RIS), a hospital information system (HIS) or to an internal or external network, so that others at different locations may gain access to the raw or processed image data.

The processor-based device 10 may include various types of components that may assist the processor-based device 10 in performing various types of tasks and operations. For example, the processor-based device 10 may include a communication component 12, a processor 14, a memory 16, a storage 18, input/output (I/O) ports 20, a display 22, and a database 24, and the like. During operation, the memory 16 may store an image review application 25 that includes a multi-parameter sampling tool 26 that, when executed by the processor 14, identifies one or more values or measurements derived from a selected region of interest (ROI), and automatically configure one or more parameters for one or more workflow tools. To this end, the multi-parameter sampling tool 26 may 26 may include, access, or be updated using a machine-learning routine that may be trained based on user feedback and/or input from users within a department, an institution, a local region, or the like. As such, in some embodiments the multi-parameter sampling tool 26 may not receive or have access to data regarding patient information so as to keep such information confidential.

The communication component 12 may be a wireless or wired communication component that may facilitate communication between the processor-based device 10 and various other processor-based devices via a network, the Internet, or the like. For example, the communication component 12 may send or receive images (e.g., image data) from other workstations.

The processor 14 may be any type of computer processor or microprocessor capable of executing computer-executable code. For example, the processor 14 may be configured to receive user input, such as actions performed by the user of selecting the image review application 25, selecting an image for review within the image review application 25, selecting a workflow tool, performing one or more actions of a workflow using the workflow tool, selecting the sampling tool 26, selecting the ROI within the image with the sampling tool 26, configure one or more parameters for one or more workflow tools, scanning parameters, or the like. Thus, the user may select image data for viewing on the processor-based device 10, perform one or more actions (e.g., annotate, adjust contrast, measure, send) on the image data, and/or otherwise operate the processor-based device 10. Further, the processor 14 may be communicatively coupled to other output devices, which may include standard or special purpose computer monitors associated with the processor 14. One or more processor-based device 10 may be communicatively coupled for requesting examinations, viewing image data, sending image data, storing image data, and so forth. In general, displays, printers, workstations, and similar devices supplied with or within the system may be local to the data acquisition components, or may be remote from these components, such as elsewhere within an institution (e.g., hospital, school), or in an entirely different location, linked to the processor-based device 10 via one or more configurable networks, such as the Internet, virtual private networks, and so forth. The processor 14 may also include or be implemented as multiple processors that may perform the operations described below.

The memory 16 and the storage 18 may be any suitable articles of manufacture that can serve as media to store processor-executable code, data, or the like. These articles of manufacture may represent computer-readable media (e.g., any suitable form of short-term memory or long-term storage) that may store the processor-executable code used by the processor 14 to perform the presently disclosed techniques. As used herein, applications may include any suitable computer software or program that may be installed onto the processor-based device 10 and executed by the processor 14. The memory 16 and the storage 18 may represent non-transitory (e.g., physical) computer-readable media (e.g., any suitable form of memory or storage) that may store the processor-executable code used by the processor 14 to perform various techniques described herein. For example, the memory 16 may include machine-learning routines configured to learn the user's preferred parameter for each workflow tool and/or the user's preferred workflows for reading the image data.

The memory 16 may store a processor-executable image review application 25 including the sampling tool 26 for execution by the processor 14. The image review application 25 may also include one or more workflow tools used to review image data. The sampling tool 26, when executed, may automatically configure (e.g., suggest, set, adjust, update) one or more parameters for a workflow tool based on pixel data (e.g., pixel values, voxel data) of a selected or sampled region of the image data. For example, the sampling tool 26 may set a value for multiple parameters of a selected workflow tool. That is, the sampling tool 26 may receive user input (or additional user input) of a region of interest (ROI) within the image data, extract a subset of pixels (e.g., pixels of the ROI, voxels of the ROI), and automatically configure one or more parameters of the workflow tool based on a value or values of the subset of pixels or subset of voxels. In certain instances, the sampling tool 26 may generate one or more charts or graphs, such as bar charts, histograms, scatter plots, linear regressions, and the like based on the subset of pixels. In other instances, the sampling tool 26 may perform a statistical analysis on the pixels of the sampled region to determine a central tendency (e.g., mean, median, mode). For example, the sampling tool 26 may generate a histogram based on the subset of pixels and populate a graphical user interface (GUI) with the histogram for the user to view on the display 22 of the processor-based device 10. In another example, the sampling tool 26 may receive user input (or additional user input) to adjust a size and/or shape of the ROI and configure a parameter of the workflow tool based on the re-sized and/or re-shaped ROI. The sampling tool 26 may be trained with historical user data and/or a machine-learning model 28 stored in the database 24. As such, the sampling tool 26 may predict subsequent workflows and/or image viewing preferences of the user and automatically perform certain steps of the workflow and/or image visualization to reduce read time.

Returning to the processor-based device 10, the I/O ports 20 may be interfaces that may couple to other peripheral components such as input devices (e.g., keyboard, mouse), sensors, input/output (I/O) modules, and the like. For example, the user may use a mouse to click on one or more points within the image data to select the ROI and a keyboard to annotate on the image data. The display 22 may operate as a human machine interface (HMI) to depict visualizations associated with software or executable code being processed by the processor 14. In one embodiment, the display 22 may be a touch display capable of receiving inputs from a user of the processor-based device 10. The display 22 may be any suitable type of display, such as a liquid crystal display (LCD), plasma display, or an organic light emitting diode (OLED) display, for example. Additionally, in one embodiment, the display 22 may be provided in conjunction with a touch-sensitive mechanism (e.g., a touch screen) that may function as part of a control interface for the processor-based device 10. For example, the image review application 25 and/or the sampling tool 26 may receive user input (or additional user input) via the display 22 (e.g., a touch-screen) of a boundary of the ROI.

The processor-based device 10 may also include the database 24 that stores historical user data and the machine-learning model 28. The database 24 may store workflow data such as frequent workflow tools used by the user, parameters for one or more workflow tools, preferences of the user, and so on. The database 24 may also store parameters and each function performed by the workflow tool, respectively. In an embodiment, the database 24 may be a cloud server or a remote database that stores historical user data of multiple users. In certain instances, the database 24 may store a user profile including an institution, a department, a specialty, a credential, a seniority, and the like. The sampling tool 26 may utilize the user profile to determine one or more user preferences for reviewing the image data. For example, a user profile may indicate that the user specializes in bone density scans and the sampling tool 26 may adjust a contrast of the image data based on the specialization. In another example, an institution may streamline workflows using certain parameters and/or certain configurations for the parameters (e.g., certain parameter values) for one or more workflow tools. The sampling tool 26 may learn the parameters and automatically set the parameters based on the institution and/or a department as well as on a sampled ROI within the image. In this way, preferences across the institution and/or a department may be considered by the sampling tool 26 when configuring the parameters for one or more workflow tools.

Additionally or alternatively, the database 24 may also store data for a machine-learning model 28 utilized to train the sampling tool 26. The machine-learning model 28 may include user feedback over time (e.g., historical user data) and may be used to train the sampling tool 26 to automate the steps of extracting the subset of pixels defining the ROI, automatically configuring one or more parameters of one or more workflow tools based on the values of the subset of pixels, and automatically adjusting the image data based on the subset of pixels. The machine-learning model 28 may also be used to train the sampling tool 26 to predict user preferences and workflow habits over time. Although the illustrated machine-learning model 28, or parameters configuring the machine-learning model 28, is stored within or otherwise associated with the database 24, in an embodiment the machine-learning model 28 may be communicatively coupled to the processor-based device 10 via the network 30. Although the illustrated database 24 is stored within the processor-based device 10, in certain embodiments, the database 24 may be stored on a cloud server or may be a remote database coupled to the processor-based device 10 via a network 30.

It should be noted that the processor-based device 10 should not be limited to include the components described above. Instead, the components described above with regard to the processor-based device 10 are examples, and the processor-based device 10 may include additional or fewer components relative to the illustrated embodiment. For example, the processor 14 and the memory 16 may be provided collectively within the processor-based device 10.

In certain embodiments, the processor-based device 10 may be communicatively coupled to a network 30, which may include collections of workstations, the Internet, an Intranet system, or the like. The network 30 may facilitate communication between the processor-based device 10 and various other data sources. For example, the network 30 may facilitate communication between a processor-based device 10 located on the surgery floor and a processor-based device 10 located on the radiology floor. In another example, the network 30 may facilitate communication between the processor-based device 10 and the database 24 (e.g., a cloud server, a remote database). The database 24 may store image data (e.g., raw or processed), historical user data, one or more user profiles, and the like. Although the database 24 is illustrated as separate from the processor-based device 10, in an embodiment, the database 24 may be stored partially or wholly within the processor-based device 10. In other embodiments, as described herein, the database 24 may be a cloud service or a remote database communicatively coupled to the processor-based device 10 via the network 30. In an embodiment, the processor-based device 10 may be communicatively coupled to the machine-learning model 28. As described herein, the machine-learning model 28 may incorporate or process user feedback over time (e.g., historical user data) and may be used to train the sampling tool 26 to automate the steps of extracting the selected pixels from the ROI, automatically configuring one or more parameters of one or more workflow tools based on the subset of pixels, and automatically adjusting the image data based on the subset of pixels.

Figure 2:
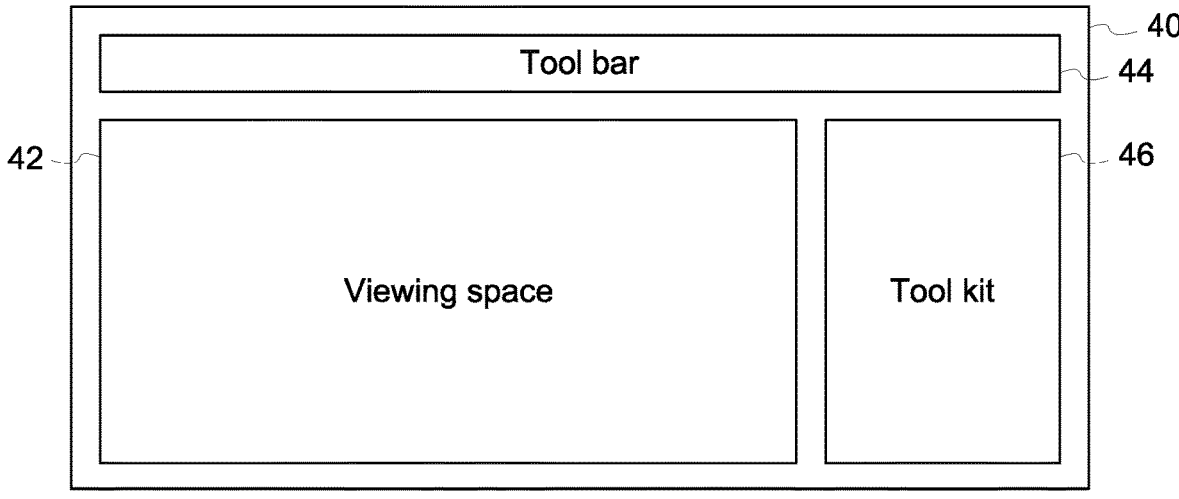
FIG. 2 illustrates a schematic diagram of a graphical user interface (GUI) generated by the image review application, such as for display on the processor-based system of FIG. 1, in accordance with aspects of the disclosure.

With the foregoing in mind, FIG. 2 is a schematic illustration of a graphic user interface (GUI) 40 displayed on the display 22 of the processor-based device 10, in accordance with aspects of the present disclosure. When executed by the processor 14, the image reviewing application 25 may display the GUI 40. The GUI 40 may include a viewing space 42 that displays image data (e.g., a medical image) for review, a toolbar 44 including an indication one or more tools (e.g., workflow tool, sampling tool 26) for selection, and a tool kit 46 including one or more parameters for a selected tool.

For example, the user may select image data for review using input devices and the image review application 25 may display the selected image data in the viewing space 42. In certain instances, the image data may be two-dimensional (2D) image data (e.g., X-ray, mammography, fluoroscopy), volumetric image data (e.g., 3D image data, magnetic resonance imaging (MRI), computed tomography (CT), single-photon emission computed tomography (SPECT), positron emission tomography (PET), tomosynthesis, ultrasound), or the like. The user may select the image data for review and the image reviewing application 25 may populate the GUI 40 with the image data in the viewing space 42. In certain implementations the image reviewing application 25 may retrieve or sample the image data from the database 24. In other implementations, the image review application 25 may receive the image data via the I/O ports 20 in real-time or near real-time. For example, the processor-based device 10 may be a C-ARM used in an operating room and the image data may be generated during an operation.

The user may select one or more tools (e.g., sampling tool 26, workflow tool) from the toolbar 44. For example, the toolbar 44 may include indications of the tools, such as a string of text, pictorial representations, buttons, and the like. For example, a button may correspond to a workflow tool, such as a contrast tool, a multi-range threshold tool, a density tool, a dose contrast tool, a vessel annotation tool, a window viewing tool, a brush tool or brush panel, a gray-scale or brightness tool, and so on. In another example, the button may correspond to the sampling tool 26.

The image review application 25 may populate the tool kit 46 with one or more parameters of a selected workflow tool. For instance, the tool kit 46 may include a configuration panel with one or more parameters of the workflow tool. The parameters may be displayed as sliders, pictorial representations, boxes, and the like in the tool kit 46. For example, the user may select the sampling tool 26 and the tool kit 46 may be populated with one or more parameters of the sampling tool 26, such as a shape or a size of the ROI, a type of analysis, and the like. Additionally or alternatively, the user may select a workflow tool for review and the image review application 25 may populate the tool kit 46 with the configuration panel the workflow tool parameters. The sampling tool 26 and/or the user may set a value for each workflow tool parameter. For example, the user may select a contrast tool and the tool kit 46 may be populated with a slider corresponding to a parameter of the contrast tool. The user may adjust an indicator on the slider to adjust a value of the parameter. For example, the slider may be associated with a brightness level and adjusting the slider may increase or decrease the brightness level applied by the contrast.

In certain instances, the sampling tool 26 may set the parameter values of a selected workflow tool based on selected pixels. To this end, the sampling tool 26 may be used to derive, determine, or specify one or more parameter values associated with the selected tool from the database 24. For example, the user may use the sampling tool 26 to define a ROI and the sampling tool 26 may extract one or more values from the subset of pixels associated with the ROI. In another example, the sampling tool 26 may extract the values from a subset of voxels associated with the ROI, such as for volumetric image data. As used herein, the term pixel or pixel data also includes the terms voxel or voxel data that is associated with volumetric image data. For example, the sampling tool 26 may receive user input (or additional user input) of a region of interest (ROI) within volumetric image data, extract a subset of voxels, perform a statistical analysis based on the subset of voxels, and automatically configure one or more parameters of the workflow tool based on a value or values of the subset of voxels. As further described with respect to FIGS. 6-9, the sampling tool 26 and/or the image review application may also populate the tool kit 46 with a graphical representation of pixels or values or distributions derived for pixels that are extracted from a selected or sampled ROI.

Based on user input (e.g., interactions with the image data in the viewing space 42), the sampling tool 26 may adjust the display or visualization of the image data, such as via dynamically configuring parameter values of the selected workflow tool. For example, the user may select an annotation tool and the sampling tool 26 may set the values of each parameter of the annotation tool based on the subset of pixels. Then, the user may select a contrast tool to adjust a contrast of the image data. In response to the user selecting the contrast tool, the image review application 25 may populate the tool kit 46 with the parameters of the contrast workflow tool and the sampling tool 26 may dynamically configure the parameter of the contrast tool. As such, the parameters of the contrast tool may be optimized prior to the user performing workflow operations. Additionally or alternatively, the sampling tool 26 may adjust the image data by applying a mask (e.g. layer) to the image data or may directly adjust the pixel values associated with the image data based on the configured contrast tool. The sampling tool 26 may based on the subset of pixels sampled, increase a brightness of the image data by automatically shifting an indicator on the first slider. In another example, the sampling tool 26 may decrease a brightness of the image data by automatically shifting the associated indicator. In this way, the sampling tool 26 may reduce a number of steps of the workflow performed by the user. In this way, the sampling tool 26 may dynamically configure one or more parameters of the selected workflow tool and/or dynamically adjust the image data.

In certain instances, the sampling tool 26 may automatically configure one or more parameters of the selected workflow tool and the user may adjust the parameters. For example, the user may select a contrast tool from the toolbar 44 and the tool kit 46 may be populated with the configuration panel with parameters of the contrast tool. The contrast tool may include three parameters, such as a first parameter for image brightness, a second parameter for image contrast, and a third parameter for image highlighting. As such, the configuration panel may include a first slider for image brightness, a second slider for image contrast, a third slider for image highlighting, and the like. The user may adjust the parameters by interacting with the configuration panel. For example, the user may adjust the image contrast value by sliding the indicator on the second slider and adjust a highlight value by sliding the indicator on the third slider. In certain instances, the configuration panel may include one or more input boxes associated with the one or more parameters. As such, the user may input a value for the parameter. For example, the user may increase the contrast value to 50 by inputting the value 50 into the input box. As described herein, the sampling tool 26 may learn user preferences from the user feedback and predict future parameter values for the workflow tool, thus improving workflow operations and decreasing turn-around time.

Figure 3:
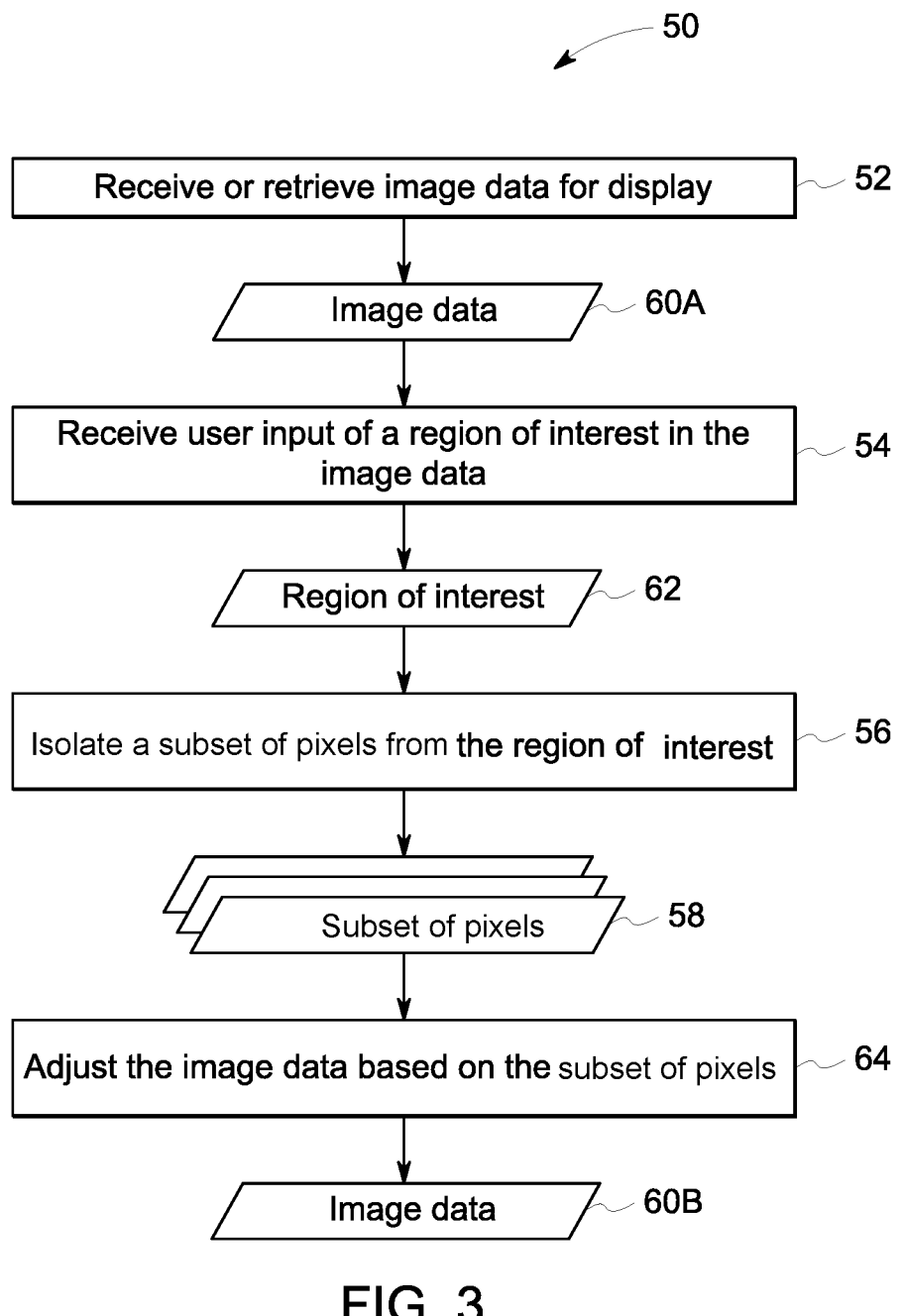
FIG. 3 illustrates a flow chart of an example method for adjusting image data displayed on the processor-based system of FIG. 1 based on a subset of pixels, in accordance with aspects of the disclosure.
Figure 4:
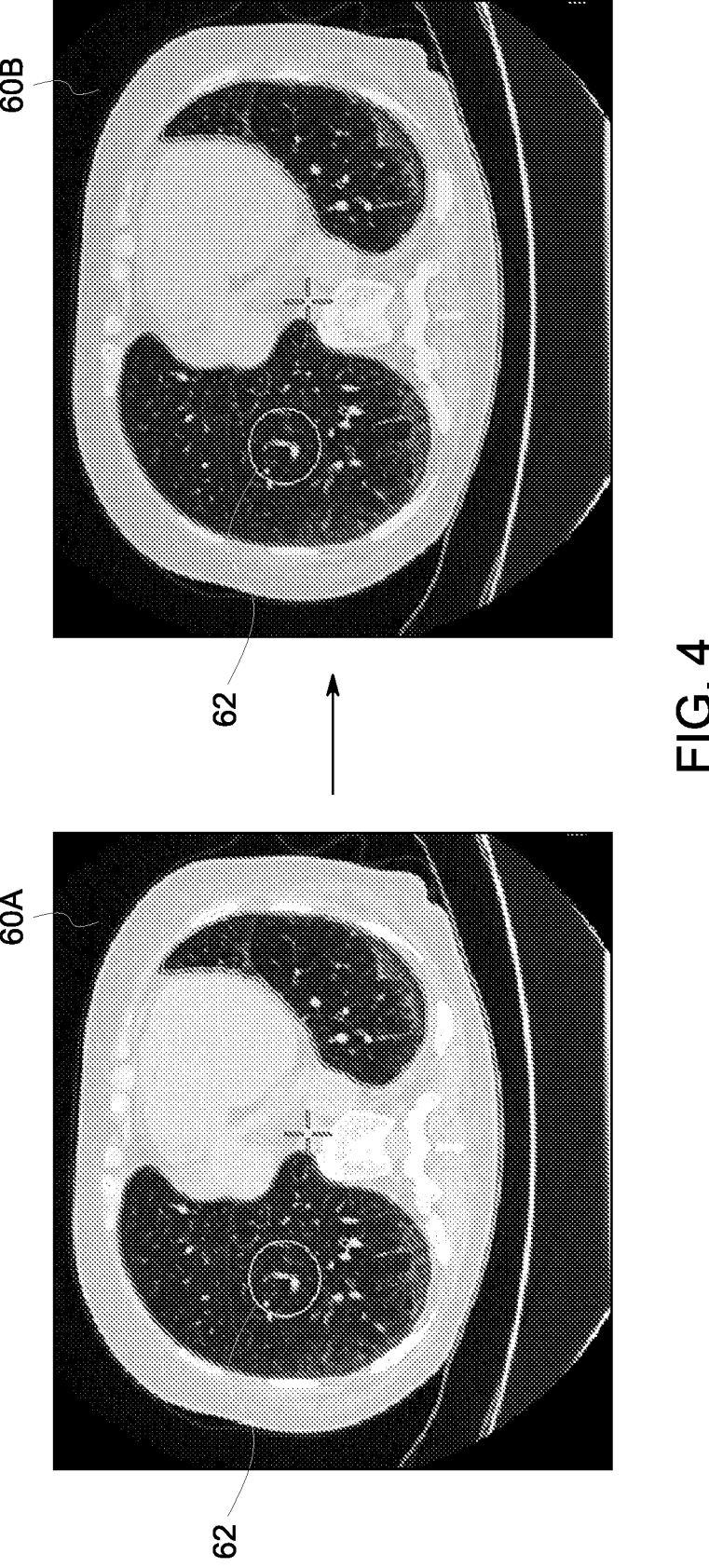
FIG. 4 illustrates example images depicting the adjustment of image data using a sampling tool, in accordance with aspects of the disclosure.

FIG. 3 is a flowchart of an example method 50 for adjusting (e.g., manipulating) image data based on the subset of pixels of the ROI selected using the sampling tool 26, in accordance with aspects of the disclosure. FIG. 4 is a schematic illustration of image data 60 displayed on the processor-based device 10, in accordance with aspects of the disclosure. To facilitate discussion, FIGS. 3 and 4 are described together.

At block 52, the image review application 25 may receive or retrieve image data for display. For example, the user may select image data for reviewing from the toolbar 44 and the image review application 25 may populate the viewing space 42 with the image data 60 in response to receiving the user input. As illustrated in FIG. 4, the image data 60A is a CT scan of a patient's chest. In certain instances, the image review application 25 may retrieve the image data 60A from the database 24. In other instances, the image review application 25 may receive the image data 60A from an input device coupled to the I/O ports 20 of the processor-based device 10. For example, the processor-based device 10 may be on an operating floor, and the image data 60A may be generated in real-time or near real-time during an operation. As such, the users may view the selected anatomy in the viewing space 42 and adjust the image data 60A during the operation. In another example, the processor-based device 10 may be in a clinic or an out-patient setting, and the image data may be generated in real-time or near real-time by one or more input devices.

At block 54, the image review application 25 may receive user input selecting a region of interest 62 within the image data 60A. For example, the user may use the sampling tool 26 to define a ROI 62 within the image data 60 using the sampling tool 26 by user input, such as clicking a mouse or touching a screen. In certain instances, the ROI 62 may include ten-pixels for the application 25 to determine a robust estimation of mean and standard deviation. In other instances, the ROI 62 may include one hundred pixels or more. Still in other instances, the pixel data of the ROI 62 may be multi-dimensional data, such as voxel data. For example, the displayed CT scan may be a slice of volumetric image data and the sampling tool 26 may extract image data from adjacent or proximate slices for additional pixel or voxel data. In this way, the sampling tool 26 may generate a multi-dimensional ROI 62 from 2D or 3D image data. In another example, the user may select a shape (e.g., circle, square, oval, diamond) for the sampling tool 26 to define the shape for the selected ROI 62. As illustrated, the ROI 62 within the image data 60A is a 2D circle. In certain instances, the image data 60 may be a 3D image and the user may select a 3D shape, such as a cube, a sphere, or any suitable 3D shape to define the ROI 62. Still in another example, the user may define a segmented organ and/or an anatomical prior and the sampling tool 26 may constrain the user to the shape of the selected anatomy to define the ROI 62. As further described with respect to FIG. 10, the user may change a size of the ROI 62 by user input, such as interacting with the tool kit 46, spinning a scroll wheel of the mouse, holding down a right mouse button or a left mouse button, and the like. In other instances, the user may select a subsequent ROI by selecting multiple points within the image data 60A. The sampling tool 26 may connect each of the points to define the ROI 62.

At block 56, the image review application 25 may extract (e.g., identify) a subset of pixels 58 associated with (e.g., within) the region of interest 62. For example, the sampling tool 26 may isolate the subset of pixels 58 associated with the ROI 62 and determine one or more values for each pixel in the subset of pixels 58. The sampling tool 26 may determine a spectral value, a color, a brightness, an intensity, a color value, a density, an attenuation factor (from unprocessed pixel data), and the like from the subset of pixels 58. In another example, the image data 60A may be an X-ray image and the sampling tool 26 may extract an absorption at a frequency, a noise level, and the like from the subset of pixels 58. Still in another example, the sampling tool 26 may perform a statistical analysis with the values of the subset of pixels 58 to determine a central tendency (e.g., a mean, a median, a mode, range), a linear regression, a standard deviation, a percentile, and the like. In certain instances, the sampling tool 26 may filter the image data locally to adjust the subset of pixels 58 before performing the statistical analysis. As further described with respect to FIGS. 6-9, the sampling tool 26 may generate a histogram based on the subset of pixels 58. For example, the sampling tool 26 may create a granulometry histogram to determine a size of selected anatomy. Additionally or alternatively, the sampling tool 26 may provide a characterization of the histogram using expectation maximization (EM) routines or iterative full width at high maximum (FWHM) estimation. In certain instances, the sampling tool 26 may populate the tool kit 46 of the GUI 40 with the histogram and/or the characterization for display and review on the processor-based device 10.

At block 64, the image review application 25 may adjust (e.g., manipulate) the image data 60A based on the subset of pixels 58 or with a characterization of the subset of pixels 58 to create an adjusted image 60B. As illustrated in FIG. 4, the sampling tool 26 may enhance a brightness or a contrast of the image data 60A to create the image data 60B based on the ROI 62. For example, the ROI 62 may include a bone and the sampling tool 26 may adjust a contrast of the image data 60A based on subset of pixels 58 associated with the bone. As such, the user may see a clear visualization of the bone (and any fractures) but may not see a clear visualization of tissues surrounding the bone. If the user wants to view the surrounding tissues, then the user may define a new ROI with the sampling tool 26 and the sampling tool 26 may adjust the image data based on the newly defined ROI. In another example, the sampling tool 26 may adjust a window width or a window level to create the adjusted image data 60B. In certain instances, the sampling tool 26 may adjust one or more pixel values of the image data 60 to create the adjusted image 60B. In another example, the sampling tool 26 may apply a mask and/or a layer to modify the image data 60A and create the adjusted image data 60B. Still in another example, the sampling tool 26 may create the adjusted image data 60B based on the user profile. For example, the user profile may include user preferences such as a brightness level, a contrast level, or the like and the sampling tool 26 may automatically apply the user preferences to the image data 60A to adjust each pixel value and create the adjusted image data 60B.

Although the method 50 is described in a particular order, it should be noted that the method 50 may be performed in any suitable order and is not limited to the order presented herein. It should also be noted that although each block is described with respect to the method 50 as being performed by the image review application 25 and/or the processor-based device 10, other suitable processor-based devices (e.g., cloud server, webpage, tablet, mobile device, etc.) may perform the methods described herein. For example, the method 50 may be performed on the front end (e.g., the processor-based device 10, webpage, browser, etc.) to adjust image data based on a subset of pixels. In another example, the method 50 may be performed on the back end (e.g., remote server, cloud server) to adjust image data.

Figure 5:
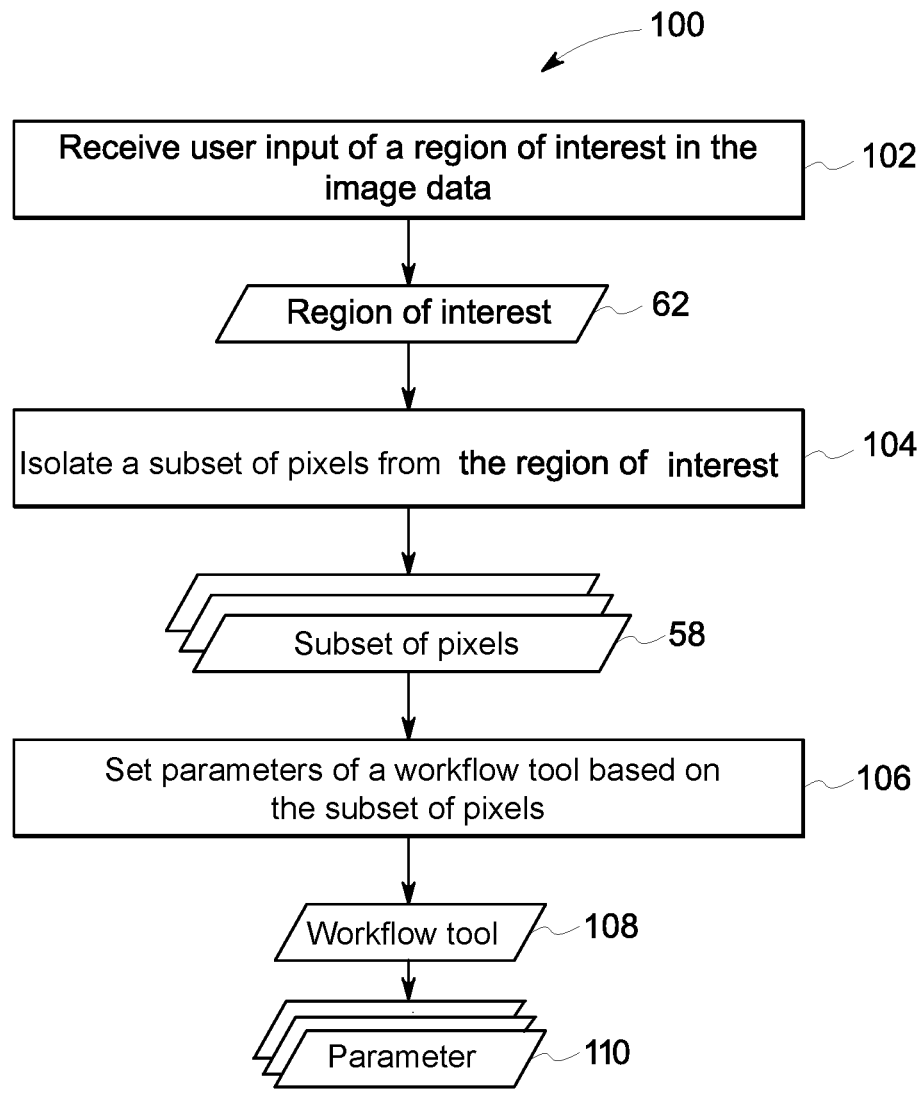
FIG. 5 illustrates a flow chart of an example method for setting or adjusting values for one or more parameters for a workflow tool, in accordance with aspects of the disclosure.

FIG. 5 illustrates a flow chart of an example method 100 for setting parameters for one or more workflow tools based on the subset of pixels 58 associated with the ROI 62, in accordance with aspects of the disclosure. As described herein, the user uses the sampling tool 26 to select the ROI 62 within the image data 60 and the sampling tool 26 may extract or select a subset of pixels 58. Based on the values and/or the characterization of the subset of pixels 58, the sampling tool 26 may configure one or more parameters of one or more workflow tools to reduce a number of workflow steps performed by the user. In this way, the sampling tool 26 may accelerate workflows for the user, decrease review time, and improve quality of service delivered.

At block 102, the image review application 25 may receive user input of a ROI 62 of the image data 60A, similar to block 54 described with respect to FIG. 3. The image data 60 may be a 2D image, a 3D image (e.g., volumetric data), an anatomical prior, and the like. At block 104, the image review application 25 may extract a subset of pixels 58 associated with the ROI 62, similar to block 56 described with respect to FIG. 3. The sampling tool 26 may also perform a statistical analysis on the subset of pixels 58 to characterize the subset of pixels 58.

At block 106, the image review application 25 may configure one or more workflow tool parameters based on the subset of pixels 58. The workflow tool 108 may be an annotation tool or a visualization tool used to manipulate perform the review. For example, the user may select a contrast tool to change an image contrast of the image data 60A. In certain instances, the sampling tool 26 may configure parameters of the contrast tool based on the subset of pixels 58. Additionally or alternatively, the user may manually adjust the parameters of the contrast tool by interactions with the tool kit 46, such as adjust an indicator on a slider, entering a numeric value, and the like. Over time, the sampling tool 26 may learn from the user adjustments to configure the workflow tool parameters 110. Additionally or alternatively, the sampling tool 26 may store the workflow tool parameters 110 the user adjusts as user preferences and/or user parameters. In certain instances, the sampling tool 26 may associate the workflow tool parameters 110 with a modality of the image data 60.

Although the steps of the method 100 are described in a particular order, it should be noted that the steps of the method 100 may be performed in any suitable order and are not limited to the order presented herein. It should also be noted that although each block is described with respect to the method 100 as being performed by the image review application 25 and/or the processor-based device 10, other suitable processor-based devices (e.g., cloud server, webpage, tablet, mobile device, etc.) may perform the methods described herein. For example, the method 100 may be performed on the front end (e.g., the processor-based device 10, webpage, browser, etc.) or the back end (e.g., remote server, cloud server) to configure one or more parameters of the workflow tool.

Figure 6:
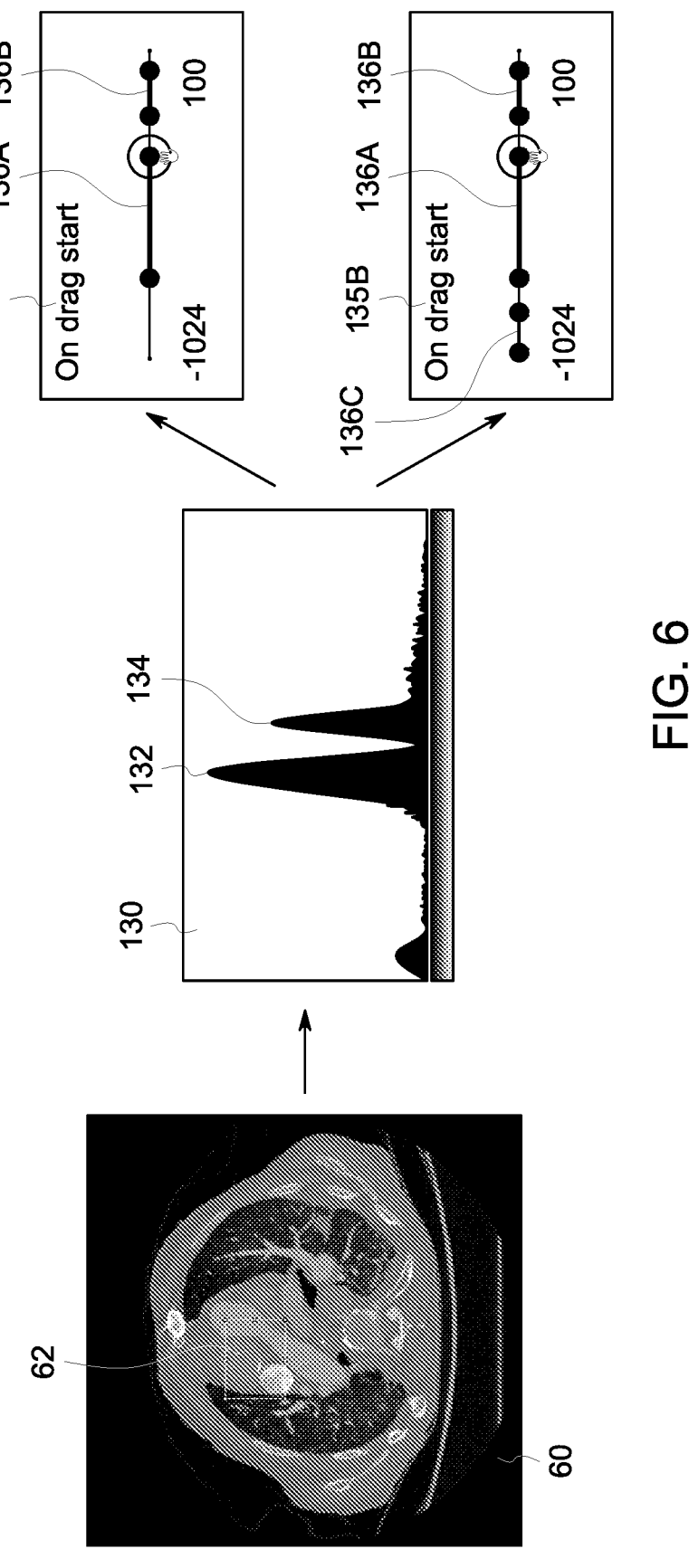
FIG. 6 illustrates a schematic diagram of a sampling tool being used to set or adjust a value for each parameter of a multi-range tool, in accordance with aspects of the disclosure.

FIG. 6 illustrates a schematic diagram of the sampling tool 26 configuring parameters of a first workflow tool (e.g., first multi-range threshold tool 108A) and a second workflow tool (e.g., second multi-range tool 108B), in accordance with aspects of the disclosure. By way of example, the multi-range threshold tool 108 may take in multiple parameters (e.g., threshold values) to manually segment tissues and a threshold level of the image. Traditionally, the user may set each of the threshold values to acquire a distribution of heart vessels and/or provide the one or more thresholds to segment the image data 60 in order to get the size of the heart vessels. As such, reviewing the image data 60 may be a time-consuming process.

However, as described herein, the user may use the sampling tool 26 to define the ROI 62 within the image data 60, dynamically extract the subset of pixels 58 from the ROI 62, and automatically configure one or more parameters of the workflow tool 108 based on the pixels within the ROI 62. In certain instances, the ROI 62 may include an anatomy or a portion of an anatomy from the image data 60. For example, the user may select the boundaries of a tumor for the purpose of measuring tumor size. In another example, the user may select the boundaries of a blood vessel.

As illustrated, the image data 60 is a CT chest image and the ROI 62 is a square defining a portion of a heart. The sampling tool 26 may isolate a subset of pixels 58 associated with the ROI 62 and perform an analysis on the subset of pixels 58 to configure the multi-range tool parameters. As illustrated, the sampling tool 26 may generate a histogram 130 based on a brightness value or a grayscale value of the subset of pixels 58. For example, the sampling tool 26 may generate a local grayscale histogram 130 from pixels 58 within the selected ROI 62. The histogram 130 includes a first histogram cluster and a second histogram cluster and the sampling tool 26 may fit a first curve 132 to the first histogram cluster and a second curve 134 to the second histogram cluster.

Additionally or alternatively, the tool kit 46 of the GUI 40 (described with respect to FIG. 2) may be populated with the histogram 130. In certain instances, the sampling tool 26 may provide a characterization of the histogram 130. For example, the histogram 130 may include a count=6603, a mean=171, a standard deviation=351, a number of bins=256, a minimum=−959, a maximum=148, a mode=138 (253) and a bin width=10. The characterization information may be displayed adjacent the histogram 130. In certain instances, the user may select one or more inputs (e.g., pixels, histogram cluster, fitted curve) to not be included in the analysis. In other instances, the user may adjust the characterization information. For example, the user may adjust the number of bins, the count, a bin width, or the like.

As such, the sampling tool 26 update the characterization and re-adjust multi-range tool parameters 110.

As described herein, the sampling tool 26 may populate the tool kit 46 of the GUI 40 with a configuration panel 135 that includes workflow tool parameters 110. For example, the first multi-range tool 108A may include two parameters, such as a first threshold value and a second threshold value. In another example, the second multi-range tool 108B may include three parameters. As illustrated, a first configuration panel 135A illustrates the two parameters of the first multi-range tool 108 with a first slider 136A and a second slider 136B. A second configuration panel 136B illustrates the three parameters of the second multi-range tool 108 with a first slider 136A, a second slider 136B, and a third slider 136C. By way of example, the sampling tool 26 may use the first curve 132 to configure parameters (e.g., threshold values) for the first multi-range tool 108A and the second curve 134 to set parameters (e.g., threshold values) for the second multi-range tool 108B. The sampling tool 26 may set a value for the first parameter 110 of the first multi-range tool 108A and adjust the value displayed by the first slider 136A. The sampling tool 26 may set a value for the second parameters 110 of the first multi-range tool 110A and adjust the value displayed by the second slider 136B. As such, the user may view the adjusted sliders 136 for a visual representation of the configured parameter. Additionally or alternatively, the sampling tool 26 may repeat the process to configure the parameters for the second multi-range tool 110B based on the second curve 134. That is, the sampling tool 26 may set a value for the first parameter, the second parameter, and/or the third parameter and populate the configuration panel 135 with a visual representation of the parameter value, such as the first slider 136A, the second slider 136B, and the third slider 136C. The application 26 may populate the tool kit 46 of the GUI 40 (described with respect to FIG. 2) with the first configuration panel 135A and/or the second configuration panel 136B. In certain instances, the user may further adjust the parameters 110 of either the first multi-range tool 108A and/or the second multi-range tool 108B by interacting with the sliders 136A and 136B and the sampling tool 26 may learn (e.g., via machine-learning routines) based on the user feedback.

In another example, the sampling tool 26 may use the first curve 132 and the second curve 134 to update parameters 110 for the second multi-range tool 108B. As illustrated, the second configuration panel 135B associated with the second multi-range tool 108B includes three parameters 110 as visually represented by the first slider 136A, the second slider 136B, and a third slider 136C. For example, the sampling tool 26 may 26 may use the first curve 132 to configure all three parameters of the second multi-range tool 108B and adjust values of the three parameters based on the second curve 134. Still in another example, the sampling tool 26 may use the first curve 132 to configure parameters for the first multi-range tool 108A and adjust the parameter value based on the second curve 134, or vice versa.

Figure 7:
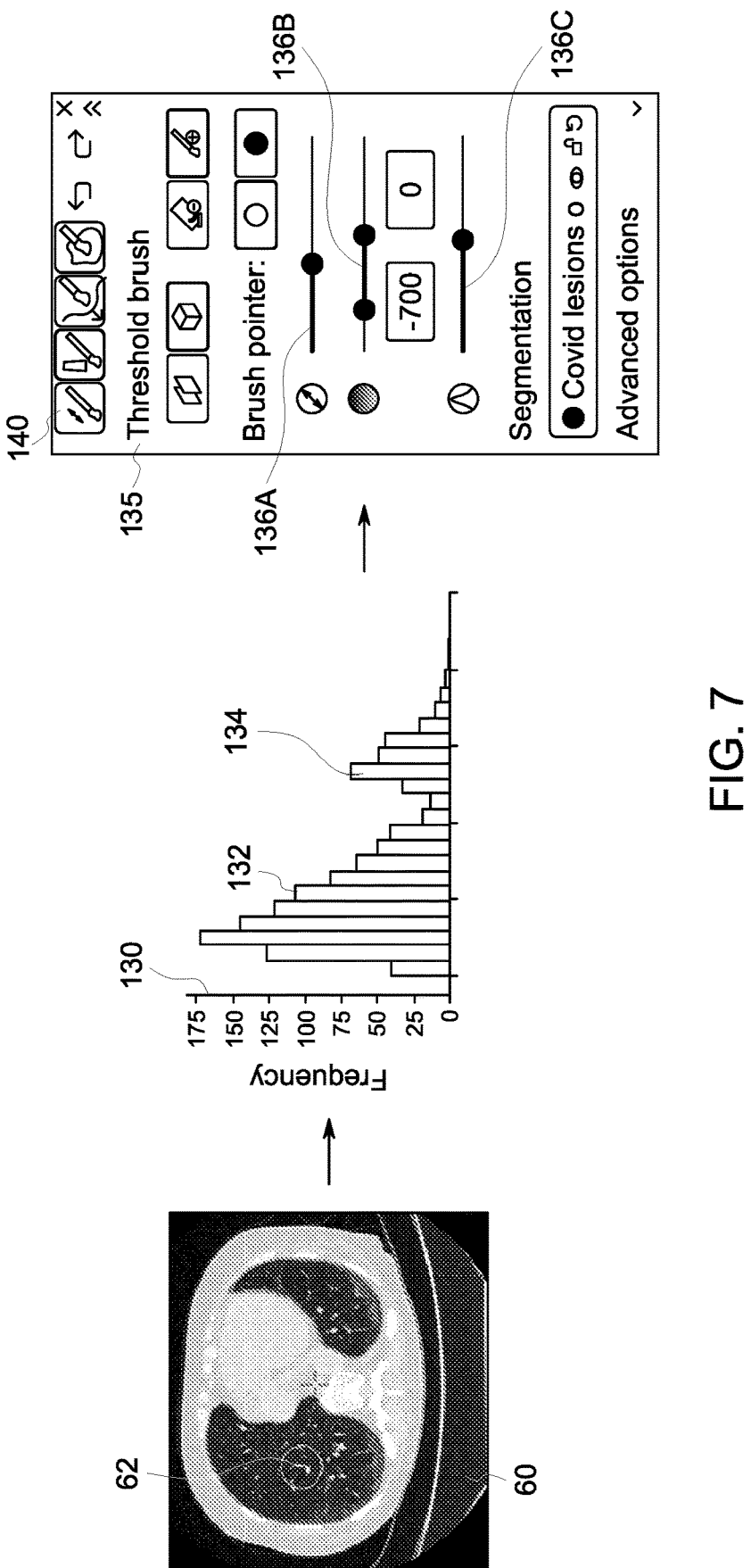
FIG. 7 illustrates a schematic diagram of a sampling tool being used to set or adjust a value for each parameter for a brush panel, in accordance with aspects of the disclosure.

FIG. 7 illustrates a schematic diagram of the sampling tool 26 configuring parameters of a workflow tool (e.g., brush panel 108), in accordance with aspects of the disclosure. By way of example, the brush panel 108 may include one or more brush tools used for dose contrast visualization, segmentation, grayscale, contrast, and the like. For example, the brush panel 108 may take in one or more parameters, such as a size for the brush, a contrast level, and a threshold value, or any combination thereof. In another example, the brush panel 108 may take in multiple parameters 110, such as a regularization size for a selected anatomy, a first threshold value for annotating the selected anatomy, and a second threshold value for annotating the selected anatomy.

As illustrated, the image data 60 is CT chest image and the ROI 62 is circle within the image data 60. As described herein, the user may use the sampling tool 26 to define the ROI 62 within the image data 60 and the sampling tool 26 may isolate a subset of pixels 58 from the ROI 62 to set values of the parameters of the brush panel 108. For example, the sampling tool 26 may perform a characterization of the subset of pixels 58 by generating the histogram 130. The histogram 130 may represent grayscale values extracted from the subset of pixels 58. In the illustrated histogram 130, the histogram 130 includes a first histogram cluster and a second histogram cluster. The sampling tool 26 may fit a first curve 132 to the first histogram cluster and a second curve 134 to the second histogram cluster. The user and/or the sampling tool 26 may determine that the first curve 132 provides a poor representation (e.g., characterization) of the subset of pixels 58 and determine that the second curve 134 provides a better representation in comparison to the first curve 132. As such, the user and/or the sampling tool 26 may use only the second curve 134 to set the parameter values. In certain instances, the user may use the sampling tool 26 to select the first curve 132 and indicate that the first curve 132 may not be used in the analysis. In another example, the sampling tool 26 may generate a pop-up notification indicating to the user that the first curve 132 is not a good representation of the subset of pixels 58 or that the second curve 134 may be a better representation and request user input for configuring the parameters based on the first curve 132. As such, the sampling tool 26 may use the subset of pixels 58 and/or the second curve 134 to configure the parameters 110 (e.g., the regularization size, the threshold value) of the brush panel 108.

As described herein, a configuration panel 135 may include visual indicators of the parameters 110 of the workflow tool 108. As illustrated, the configuration panel 135 may include one or more buttons 140 indicating different brushes of the brush panel 108. The configuration panel 135 may also include a first slider 136A associated with the regularization size, a second slider 136B associated with the first threshold value, and a third slider 136C associated with the second threshold value. The sampling tool 26 may 26 may characterize the second curve 134 using an EM algorithm or an FWHM estimation to configure the values of the first parameter, the second parameter, and the third parameter. The configuration panel 135 may be updated with adjusted indicators for the first slider 136A, the second slider 136B, and/or the third slider 136C. For example, the sampling tool 26 may increase the value of the regularization size and adjust an indicator on the first slider 136A to the right. In another example, the sampling tool 26 may decrease the value of the first threshold and adjust an indicator on the second slider 136B to the left. In certain instances, the user may adjust the sliders 136 to adjust the parameters of the brush panel 108 by interacting with the configuration panel 135. For example, the user may adjust an indicator on the third slider 136C to the left or right to adjust the parameter. In another example, the user may adjust an indicator on the third slider 136C up or down. Still in another example, the user may enter a value into an input box associated with the parameter to adjust the value. In this way, the sampling tool 26 may learn user preferences based on the feedback.

Figure 8:
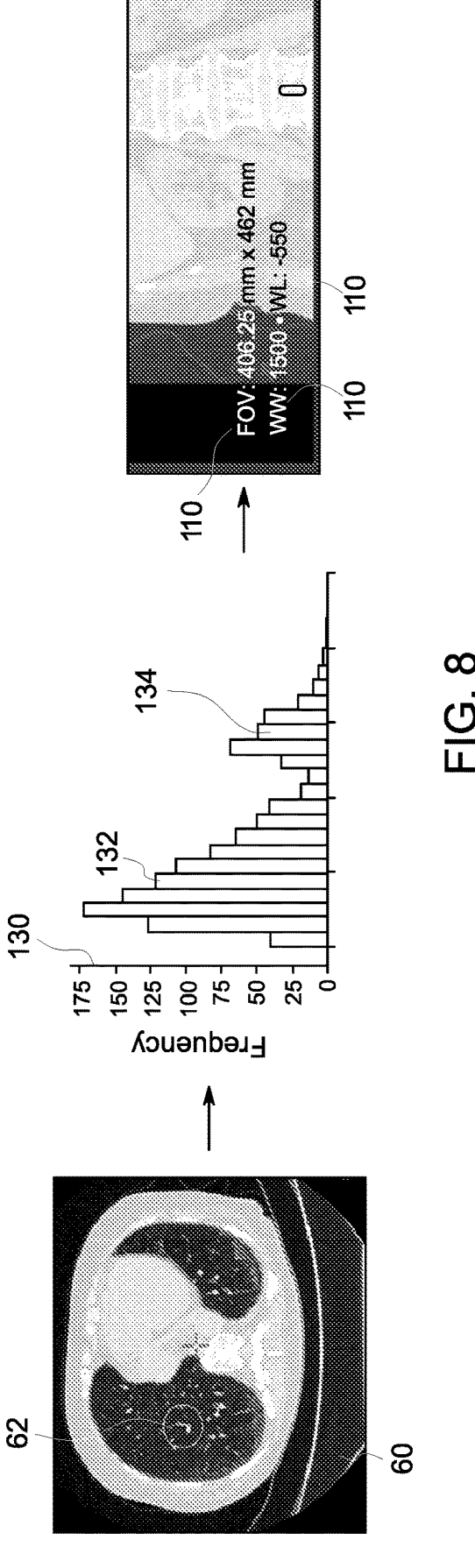
FIG. 8 illustrates a schematic diagram of a sampling tool being used to set or adjust a value for each parameter of a windowing tool, in accordance with aspects of the disclosure.

FIG. 8 illustrates a schematic diagram of the sampling tool 26 configuring parameters of a workflow tool (e.g., windowing tool 108), in accordance with aspects of the disclosure. For example, the windowing tool 108 that modi-
fies the image data 60 to highlight selected anatomy and/or
adjust a field of view (FOV). The windowing tool 108 may
have one or more parameters 110, such as window level, a
window width, and the like, which cause the FOV to change.
For example, a brightness level of the image data is adjusted
via a window level (WL) value and a contrast level of the
image data is adjusted via a window width (WW) value. The
window level value may be a midpoint of the range of values
in the window width. The window width values may include
a range of CT pixel values displayed within the image data
60. A wide window width may be useful for differing
attenuation values (e.g., boned and soft tissue), while a
narrow window width may be useful for areas of similar
attenuation values (e.g., soft tissue). In certain instances,
selected anatomy may have predefined parameters for the
windowing tool 108. By way of illustrative example, win-
dowing parameters for a brain image may be WW: 70-90,
WL: 35-50, parameters for a lung image may be WW: 1500,
WL: −600, and parameters for a bone image may be WW:
1500, WL: 550. The units of the window level and the
window width may be in Hounsfield units (Hu). Although
the illustrated windowing tool 108 is applied to a CT image,
the windowing tool 108 may also be applied to MRI images,
PET images, SPECT images, or any suitable medical imag-
ing modality.

As described herein, the user may use the sampling tool
26 to define the ROI 62 and the sampling tool 26 may isolate
the subset of pixels 58 associated with the ROI 62. The
sampling tool 26 may generate a histogram 130 based on the
subset of pixels 58, and in certain instances, the sampling
tool 26 may remove portions of the histogram 130 and/or
one or more pixels from the final characterization. For
example, the histogram 130 includes a first curve 132 and a
second curve 134. The sampling tool 26 may only perform
a characterization on the second curve 134 in response to
determining that the second curve 134 is a better represen-
tation of the ROI 62.

Based on the analysis of the subset pixels 58, the sampling
tool 26 may configure the parameters of the windowing tool
108. For example, the sampling tool 26 may 26 may
determine the window width value based on a range of the
values of the subset of pixels 58 and the window level value
based on a mean or a model of the subset of pixel data 58.
In another example, the sampling tool 26 may perform an
estimation of a mean and a standard deviation of pixels
within the second curve 134. Then, the sampling tool 26 may
26 may use a mean to determine the window level value and
one or more standard deviations to determine the window
width value. Still in another example, the user may select an
anatomy within the image data 60 and the sampling tool 26
may configure the parameters of the windowing tool 108
based on the selected anatomy. That is, the database 24 may
24 may include one or more predefined parameter values
corresponding to certain anatomy. Additionally or alterna-
tively, the sampling tool 26 may further adjust the param-
eters of the windowing tool 108 based on the subset of pixels
58. In this way, the sampling tool 26 may provide an optimal
visualization of the image data for the user to make a
diagnosis and/or write a report.

Additionally or alternatively, the sampling tool 26 may
also create the adjusted image data 60B based on the subset
of pixel data 58 and populate the viewing space 42 with the
adjusted image data 60B. For example, the sampling tool 26
may automatically adjust a brightness level, a contrast, a
grayscale level, and the like of the image data 60A to create
the adjusted image data 60B. To this end, the sampling tool

26 may apply a mask (e.g., filter) to the image data 60A
and/or alter the values of the pixel data of the image data
60A to create the adjusted image data 60B. As such, the user
may fewer steps of the workflow, decrease an amount of
time needed to review an image, and so on.

Figure 9:
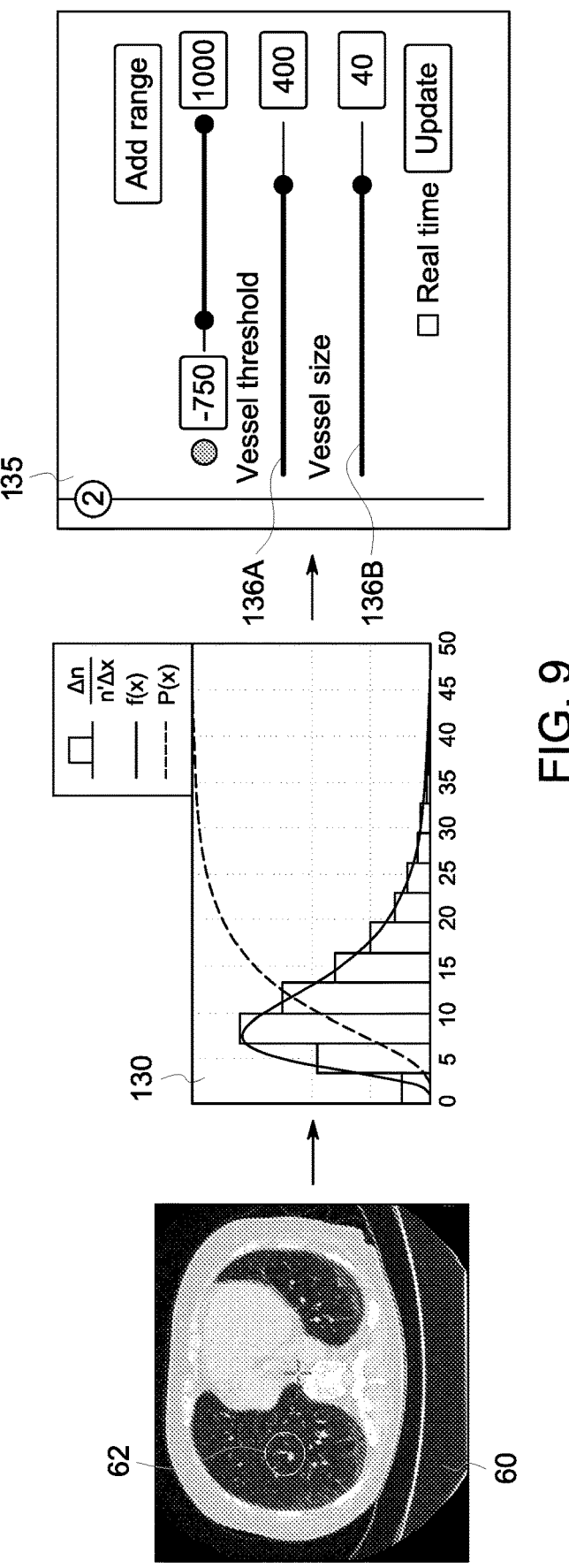
FIG. 9 illustrates a schematic diagram of a sampling tool being used to set or adjust a value for each parameter of a vessel annotation tool, in accordance with aspects of the disclosure.

FIG. 9 illustrates a schematic diagram of the sampling
tool 26 configure parameters 110 of a workflow tool (e.g.,
vessel annotation tool 108), in accordance with aspects of
the disclosure. The vessel annotation tool 108 may include
parameters such as a global and a local threshold to annotate
one or more vessels within the image data 60. The vessel
annotation tool 108 may be used to determine a size (e.g.,
length, width, surface area) of the vessels within the image
data 60.

As illustrated, the sampling tool 26 may receive user input
of the ROI 62 and perform an analysis on the subset of pixels
58 associated with the ROI 62. For example, the sampling
tool 26 may generate a granulometry histogram 130 includ-
ing a size distribution of one or more particulates within the
image data 60. The granulometry histogram 130 may
include a distribution of morphological opening gray scale
images. For example, each opening may be seen as a sieve
or a sift where the size of a grid determines a size of structure
to filter out of the medical image. As such, structures of a
certain size (e.g., preset size, statistically significant size)
may be a highest value within the granulometry histogram
130. Additionally, the sampling tool 26 may fit a curve to the
histogram 130 and/or estimate a function based on the
granulometry histogram 130. In certain instances, the sam-
pling tool 26 may use pixels of the entire image data 60
and/or perform image analysis on the image data 60 to set
the parameters of the vessel annotation tool 108. For
example, the sampling tool 26 may generate a granulometry
histogram 130 including a size distribution of one or more
vessels within the image data 60. The size distribution may
be binned based on user defined range of values or based on
values defined by the sampling tool 26. The sampling tool 26
may also fit a first curve 132 and a second curve 134 to the
granulometry histogram 130 to generate a representative
equation for the data. In certain instances, the sampling tool
26 may perform a characterization of the granulometry
histogram 130 to determine an average size of the vessels,
a main size of the vessels, a range of values, and so on.
However, in other instances, the sampling tool 26 may
provide a main size of a selected anatomy based the granu-
lometry histogram 130.

In certain instances, the blood vessels may be irregularly
shaped and the histogram 130 may include a large distribu-
tion of vessel sizes. As such, the sampling tool 26 may apply
one or more filters to the image data 60 to identify a vessel
size that is a good representation of the ROI 62. In another
example, the sampling tool 26 may fit the first curve 132 and
the second curve 134 to the histogram 130 to determine the
representative vessel size. As illustrated, a configuration
panel 135 for the vessel tool 108 may include two param-
eters represented by a first slider 136A and a second slider
136B. The first parameter may be a vessel threshold, as
represented by the first slider 136A, and the second param-
eter may be a vessel size, as represented by the second slider.
The sampling tool 26 may configure the parameters for the
vessel tool 108 and adjust the sliders 136 of the configura-
tion panel 135 to visually indicate the parameter values for
the user. Additionally or alternatively, the sampling tool 26
may populate an input box 142 of the configuration panel
135 with the parameter value. As illustrated by the first input
box 142A, the sampling tool 26 may configure the vessel
threshold to 400 Hu, and as illustrated by the second input box 142B, the sampling tool 26 may configure the vessel size to 40 millimeters (mm). As such, the sampling tool 26 may automate the process of determining one or more parameters for the vessel, thereby reducing an amount of time needed by the user to complete the review and/or make a diagnosis.

Figure 10:
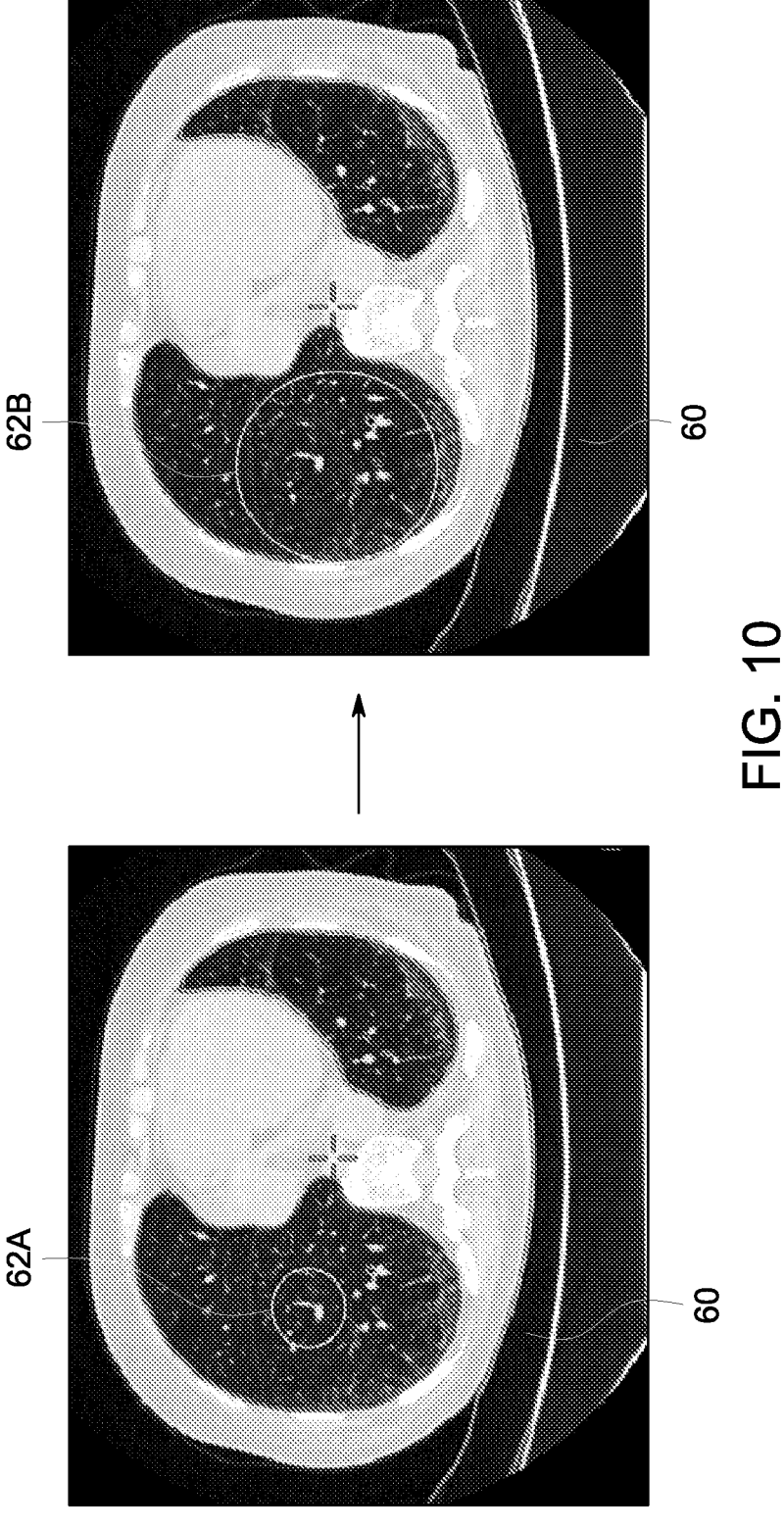
FIG. 10 illustrates example images depicting the adjustment of the size of a region of interest associated with a sampling tool, in accordance with aspects of the disclosure.

In certain instances, the image data 60 may be a three-dimensional (3D) slice and an adjacent slice may contain useful images. The sampling tool 26, via machine learning routines, may identify a subsequent or adjacent slice as containing useful image data (e.g., selected anatomy such as vessels). The image review application 25 may provide an indication to the user on the GUI 40 of the additional image data and request user input to display the additional image data. In this way, the sampling tool 26 may improve workflow operations. FIG. 10 illustrates a schematic diagram of the sampling tool 26 adjusting a size of the ROI 62, in accordance with aspects of the disclosure. As described with respect to FIG. 3, the user may select the ROI 62 by user input (e.g., mouse click, touch). The user may define a first ROI 62A in the image data 60 but then decide to adjust a size of the ROI, a location of the ROI, and the like. In this way, the user may define a second ROI 62B. As illustrated, the size of the second ROI 62B is larger than a size of the first ROI 62A. However, in other instances, the user may decrease a size of the ROI, change a shape of the ROI, change an area of the ROI, and so on. For example, the user may also change the ROI 62 by moving the defining region (e.g., circle, square, sphere, cube, user defined area). In this way, the user may define a new ROI and the sampling tool 26 may update or adjust one or more parameters for the tools and/or the image data 60. Additionally or alternatively, the user may adjust the ROI 62 to cause the sampling tool 26 to repeat the process of extracting pixels 58, configuring one or more parameters, and/or adjusting the image data. In this way, the user may train the sampling tool 26 to perform the process based on user feedback, which may be associated with user preferences.

As described herein, a configuration panel 135 of the sampling tool 26 may 26 may include parameters for the sampling tool 26, such as a size or a shape for defining the ROI 62. To this end, the configuration panel 135 may include indicators associated with each parameter of the sampling tool 26. For example, the user may interact with a slider to adjust a size of the ROI 62. Additionally or alternatively, the user may adjust the size of the ROI 62 by spinning a scroll wheel of the mouse, holding down a right mouse button or a left mouse button, and the like. For example, the user may scroll up on a ball of the mouse to increase the size of the ROI 62. In another example, the user may provide extended user input, such as holding a button of the mouse down for a threshold period of time (e.g., long click), to increase a size of the ROI 62. Still in other example, the user may select the ROI 62 by touching the display 22 (e.g., touch screen) and adjust a size of the ROI 62 by interaction time, such as a long touch. Additionally or alternatively, the user may scroll up or down on the ball of the mouse, hold a button down on the mouse, and/or interact with a touch screen to decrease the size of the ROI 62. In this way, the sampling tool 26 may automatically adjust a size of the ROI 62 based on the user input. Accordingly, the sampling tool 26 may reduce a number of steps of the workflow manually performed by the user.

Figure 11:
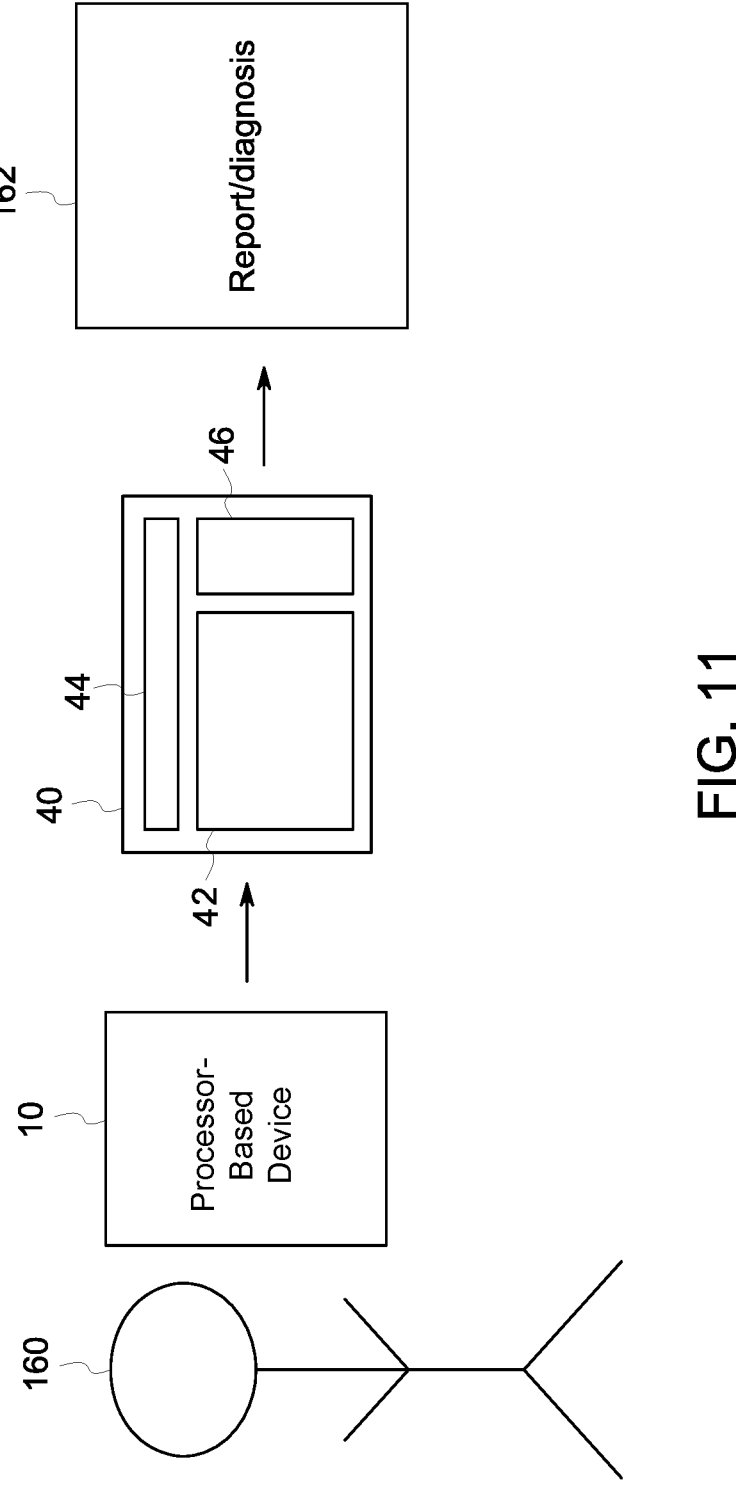
FIG. 11 illustrates a schematic diagram of a user operating the processor-based system of FIG. 1 to make a diagnosis and/or report, in accordance with aspects of the disclosure.

FIG. 11 illustrates a schematic diagram of a user 160 operating the processor-based device 10 including the image review application 25 with the sampling tool 26 to review an image and make a diagnosis, in accordance with aspects of the disclosure. The user 160 may operate the processor-based device 10 to perform workflows including reviewing image data, annotating image data, sending image data, and so on. To this end, the processor-based device 10 includes the image reviewing application 25 including the sampling tool 26 and the one or more workflow tools 108 to perform the review. In certain instances, the user 160 may perform workflow operations on any suitable processor-based device, such as a tablet, a mobile device, a personal laptop, and so on. In this case, the image review application 25 and/or the sampling tool 26 may be executed by a cloud server or remote server communicatively coupled to the processor-based device 10.

The processor-based device 10 may display the GUI 40 including the viewing space 42, the toolbar 44, and the tool kit 46. The user may select image data 60 for review by interacting with the GUI 40. The user may then select the sampling tool 26 to streamline certain workflow operations. The sampling tool 26 may automate the process extracting the subset of pixels 58 from a region of interest 62, configuring parameters for one or more workflow tools 108, adjusting the image data 60, and/or characterizing the subset of pixels 58. The sampling tool 26 may also be a multi-modality tool and be used for a variety of modalities, such as CT, MR, GSI, XA, interventional radiology, and so on. The sampling tool 26 may also be applied to image segmentation tools, image reconstruction tools (e.g., in 3D or 2D), measuring tools (e.g., 1 point sampling, line intensity and distance measurements, 2D region selection and sampling, 3D volume measurement), transform tools (e.g., spatial transformation, image correction), image processing tools (e.g., histogram manipulation, morphological operations, image filtering and enhancement), display tools (e.g., advance image visualization and volume rendering). The sampling tool 26 may also be applied to image registration tools for aligning one or more images, retrieving target images and/or source images for alignment, and the like. The sampling tool 26 may also be applied to tools for registration of data as well as multi-modality image fusion.

As such, the sampling tool 26 may extract information from the image data and use the information to configure parameters for one or more workflow tools 108. The sampling tool 26 may also improve analysis and visualization workflows by adjusting the image data 60 and optimizing a field of view of the image data 60. Additionally, the sampling tool 26 may store customized parameters for the user and/or parameters associated with a modality of the image data, an anatomy, an institution, and so on. The sampling tool 26 may apply the parameters for the user, thereby improving reducing a number of workflow steps performed by the user. As such, turn-around time may decrease. For example, an amount of time taken to make a diagnosis and/or generate a report 162 may decrease.

Technical effects of the disclosed embodiments include providing systems and methods that automatically extract multiple measurements (e.g., pixels, pixel values) from the image data, characterize of the measurements, and configure one or more parameters of one or more tools. Using the characterization, the technique may determine optimal parameters for viewing the image data, adjusting the image data, and also adjusting the image data. For example, determining a size representative of anatomy within the image data may automate the process of setting one or more parameters of an annotation tool. In another example, determining a range of pixel values may automate the process of setting a window width value and a window level value for visualization of the image data. In this way, optimal parameters for the workflow tools may be configured without user interaction. As such, a user may be able to review image data quickly, more efficiently, and with less human error. That is, the user may need less time to review the image data, make a diagnosis and/or generate report.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system, comprising:
a processor-based device storing or accessing a medical imaging review application, which when executed by the processor-based device, causes acts to be performed comprising:
retrieving medical imaging data for populating a graphical user interface (GUI) displayed on the processor-based device;
receiving a first user input selecting a workflow tool; and
receiving a second user input of selecting a sampling tool, wherein the sampling tool, when executed by the processor-based device, causes acts to be performed comprising:
receiving a third user input via the sampling tool of a region of interest within the medical imaging data;
determining a value or values for a parameter of interest based on pixels or voxels within the region of interest, wherein determining the value or values for the parameter of interest comprises:
generating a histogram based on the pixels or the voxels within the region of interest;
fitting a first curve to a first histogram cluster of the histogram;
fitting a second curve to a second histogram cluster of the histogram; and
determining the value or values for the parameter of interest based on the first curve;
adjusting the value or values for the parameter of interest based on the second curve; and
automatically configuring the workflow tool based on the determined value or values for the parameter of interest;
generating preset parameters of the workflow tool; and
using the configured workflow tool to adjust the display of the medical imaging data on the GUI.

2. The system of claim 1, wherein the sampling tool, when executed by the processor-based device, causes acts to be performed comprising:
performing a robust statistical analysis on the pixels or the voxels within the region of interest to determine a measure of central tendency; and
determining the value or values for the parameter of interest based on the statistical analysis.

3. The system of claim 1, wherein the sampling tool, when executed by the processor-based device, causes acts to be performed comprising:

determining the value or values for the parameter of interest in response to determining a histogram cluster of the histogram is representative of the pixels or the voxels within the region of interest.

4. The system of claim 1, wherein the sampling tool, when executed by the processor-based device, causes acts to be performed comprising:
applying a filter or filters to the pixels or the voxels of the medical imaging data prior to determining the value or values for the parameter of interest.

5. The system of claim 1, wherein the medical imaging review application, when executed by the processor-based device, uses the configured workflow tool to adjust the display of the medical imaging data by:
applying one or more masks to the medical imaging data based on the configured workflow tool; and
populating the GUI with the medical imaging data and the one or more applied masks.

6. The system of claim 1, wherein the medical imaging review application, when executed by the processor-based device, causes acts to be performed comprising:
displaying a two-dimensional representation of the medical imaging data on the processor-based device, wherein the medical imaging data comprises volumetric image data, wherein the two-dimensional representation of the medical imaging data comprises a slice of the volumetric image data;
and wherein the sampling tool, when executed by the processor-based device, causes acts to performed comprising:
identifying one or more adjacent slices of volumetric image data of the two-dimensional representation of the image data; and
determining the value or values for the parameter of interest based on the voxels of the two-dimensional representation of the image data and the adjacent slices of volumetric image data.

7. A method, comprising:
receiving, via a processor, a medical image for populating a graphical user interface (GUI) to display for a user;
receiving, via the processor, a first user input selecting a sampling tool;
receiving, via the processor, a second user input from the sampling tool of a region of interest within the medical image;
determining, via the processor, a value or values for a parameter of interest based on pixels or voxels within the region of interest, wherein the determining the value or values for the parameter of interest comprises:
generating, via the processor, a histogram comprising the pixels or the voxels of the region of interest; and
performing, via the processor, a characterization of the histogram to determine the value or values for the parameter of interest, wherein performing the characterization comprises:
fitting, via the processor, a first curve to a first histogram cluster and a second curve to a second histogram cluster of the histogram;
determining, via the processor, the value or values for a first parameter of interest based on the pixels of the first curve; and
determining, via the processor, the value or values for a second parameter of interest based on the pixels or the voxels of the second curve;
populating, via the processor, the GUI with one or more sliders associated with the value or values of the parameter of interest;

receiving, via the processor, a third user input to adjust the
one or more sliders; and storing, via the processor, the third user input and the
parameter of interest in machine-learning model;

automatically configuring, via the processor, a workflow
tool based on the adjusted value or values for the
parameter of interest; and applying, via the processor, the configured workflow tool
to adjust the display of the medical image on the GUI.

8. The method of claim 7, comprising:

receiving, via the processor, a fourth user input from the
sampling tool to adjust a size or a location of the region
of interest within the medical image; and determining, via the processor, the value or values for the
parameter of interest based on the pixels or the voxels
within the adjusted region of interest.

9. The method of claim 7, comprising:

applying, via the processor, one or more masks to the
medical image based on the configured workflow tool;
and populating, via the processor, the GUI with the medical
image and the one or more masks.

10. The method of claim 7, comprising:

receiving, via the processor, a fourth user input from the
sampling tool selecting an anatomical region within the
medical image;

determining, via the processor, the value or values for the
parameter of interest based on the anatomical region;
and adjusting, via the processor, the value or values of the
parameter of interest based on the pixels or the voxels
of the anatomical region.

11. A non-transitory, computer-readable medium compris-
ing computer-readable code, that when executed by one or more processors, causes the one or more processors to
perform operations comprising:

receiving image data for populating a graphical user
interface (GUI) to display for a user;

receiving a user input selecting a workflow tool and a
sampling tool;

receiving an additional user input from the sampling tool
of an anatomical region within the image data;

determining a value or values for a parameter of interest
based on pixels or voxels associated with the anatomi-
cal region, wherein determining the value or values for
the parameter of interest comprises:

generating a histogram comprising the pixels or the
voxels of the anatomical region;

characterizing of the histogram to determine one or
more values of a central tendency of the pixels or the
voxels of the anatomical region; and populating the GUI with the histogram, the one or more
values of the central tendency, or both;

dynamically configuring the workflow tool based on the
determined value or values for the parameter of inter-
est; and implementing the configured workflow tool to adjust the
display of the image data on the GUI.

12. The non-transitory computer-readable medium of
claim 11, wherein the operations comprises:

identifying a first histogram cluster and a second his-
togram cluster of the histogram;

determine the first histogram cluster is representative of
the pixels of the anatomical region; and characterizing the first histogram cluster to determine
the one or more values of the central tendency of the
pixels or the voxels of the anatomical region.

* * * * *